US008440214B2

(12) United States Patent
Arney et al.

(10) Patent No.: US 8,440,214 B2
(45) Date of Patent: May 14, 2013

(54) MEDICAL DEVICES FOR THERAPEUTIC AGENT DELIVERY WITH POLYMERIC REGIONS THAT CONTAIN COPOLYMERS HAVING BOTH SOFT SEGMENTS AND UNIFORM LENGTH HARD SEGMENTS

(75) Inventors: Michael Arney, Minneapolis, MN (US); Liliana Atanasoska, Edina, MN (US); Robert Warner, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1455 days.

(21) Appl. No.: 11/344,053

(22) Filed: Jan. 31, 2006

(65) Prior Publication Data

US 2007/0178136 A1 Aug. 2, 2007

(51) Int. Cl.
*A61F 13/00* (2006.01)
*C08G 63/00* (2006.01)
*C08G 73/00* (2006.01)
*C08G 79/00* (2006.01)

(52) U.S. Cl.
USPC .......................... 424/422; 528/367; 528/395

(58) Field of Classification Search ........................ None
See application file for complete search history.

(56) References Cited

U.S. PATENT DOCUMENTS

| | | | |
|---|---|---|---|
| 5,614,549 A | 3/1997 | Greenwald et al. | 514/449 |
| 6,218,016 B1 * | 4/2001 | Tedeschi et al. | 428/423.1 |
| 6,315,790 B1 * | 11/2001 | Gerberding et al. | 623/1.11 |
| 6,585,755 B2 * | 7/2003 | Jackson et al. | 623/1.15 |
| 6,627,724 B2 * | 9/2003 | Meijs et al. | 528/26 |
| 6,716,444 B1 * | 4/2004 | Castro et al. | 424/422 |
| 6,730,699 B2 | 5/2004 | Li et al. | 514/449 |
| 6,835,387 B2 * | 12/2004 | Herrmann | 424/425 |
| 7,291,166 B2 * | 11/2007 | Cheng et al. | 623/1.15 |
| 7,319,128 B2 * | 1/2008 | Ziche et al. | 528/29 |
| 7,473,417 B2 * | 1/2009 | Zeltinger et al. | 424/78.08 |
| 2002/0132072 A1 | 9/2002 | Wang et al. | |
| 2003/0224033 A1 | 12/2003 | Li et al. | 424/423 |
| 2003/0236514 A1 | 12/2003 | Schwarz | 604/890.1 |
| 2004/0096606 A1 * | 5/2004 | Lee et al. | 428/35.2 |
| 2004/0258931 A1 * | 12/2004 | Zamora et al. | 428/447 |
| 2006/0030878 A1 * | 2/2006 | Anderson et al. | 606/200 |
| 2006/0088567 A1 | 4/2006 | Warner et al. | 424/422 |
| 2006/0230476 A1 | 10/2006 | Atanasoska et al. | 623/1.15 |

FOREIGN PATENT DOCUMENTS

| | | | |
|---|---|---|---|
| DE | 102004008202 A1 * | 9/2005 | |
| WO | 99/42147 | 8/1999 | |
| WO | 02/067908 A1 | 9/2002 | |
| WO | WO 03/070807 A1 * | 8/2003 | |
| WO | 2004014449 A1 | 2/2004 | |

OTHER PUBLICATIONS

Bezemer et al. Journal of Biomedical Materials Research 2000 52:8-17.*
Deschamps et al. Biomaterials 2003 24:2643-2652.*
Park et al. Journal of Applied Polymer Science 2003 89:1505-1514.*
Ishida et al. Macromolecules 2000 33:3202-3211.*
Choi et al. Journal of the American Chemical Society 2000 122:474-480.*
Morice et al. The New England Journal of Medicine 2002 346:1773-1779.*
Sheth et al. Polymer 2003 44:743-756.*
Ahmad et al. Polymer 1997 17:4523-4529.*
Tian et al. Polymer 1996 37:3983-3987.*
M.C.E.J. Niesten et al., "Synthesis and properties of segmented copolymers having aramid units of uniform length," *Polymer*, vol. 41, 2000, pp. 8487-8500.
Bryan B. Sauer et al., "Crystalline Morphologies in Segmented Copolymers with Hard Segments of Unifrom Length," *Journal of Polymer Science: Part B: Polymer Physics*, vol. 42, 2004, pp. 1783-1792.
M.C.E.J. Niesten et al., "Tensile and elastic properties of segmented copolyetheresteramides with uniform aramid units," *Polymer*, vol. 42, 2001, pp. 6199-6207.
M.C.E.J. Niesten et al., "Segmented copolyetheresteramamids with extended poly(tetramethyleneoxide) segments," *Polymer*, vol. 42, 2001, pp. 1461-1469.
M.C.E.J. Niesten et al., "Influence of type of uniform aromatic amide units on segmented copolyetheresteramides," *Polymer*, vol. 42, pp. 931-939, 2001.
J. Krijgsman et al., "Synthesis and properties of thermoplastic elastomers based on PTMO and tetra-amide," *Polymer*, vol. 44, 2003, pp. 7573-7588.
Martijn Van Der Schuur et al., "Structure-property relations of segmented block copolymers with liquid-liquid demixed morphologies," *Polymer*, vol. 46, 2005, pp. 3616-3627.
Michael R. Hibbs et al., "Poly(ethylene terephthalate) Modified with Aromatic Bisester Diamides: Thermal and Oxygen Barrier Properties," *Journal of Polymer Science: Part A: Polymer Chemistry*, vol. 42, 2004, pp. 1668-1681.
Ehud Gazit, "A possible role for π-stacking in the self-assembly of amyloid fibrils," *The FASEB Journal*, vol. 16, 2002, pp. 77-83.
Yariv Mazor et al., "Identification and Characterization of a Novel Molecular-recognition and Self-assembly Domain within the Islet Amyloid Polypeptide," *J. Mol. Biol.*, vol. 322, 2002, pp. 1013-1024.
"Peptides self-assemble into higher order morphological structures via helical ribbon intermediates," *Heart Cut*, May 13, 2002, 2 pp.
F. Aulenta et al., "Dendrimers: a new class of nanoscopic containers and delivery devices," *European Polymer Journal*, vol. 39, 2003, pp. 1741-1771.
Neeraj Kumar et al., "Biodegradable block copolymers," *Advanced Drug Delivery Reviews*, vol. 53, 2001, pp. 23-44.

(Continued)

*Primary Examiner* — Robert A Wax
*Assistant Examiner* — Caralynne Helm
(74) *Attorney, Agent, or Firm* — Mayer & Williams PC; David B. Bonham (57) ABSTRACT

Implantable or insertable medical devices are described, which include one or more polymeric regions and one or more therapeutic agents. The polymeric regions, which regulate the release of one or more therapeutic agent from the medical device, contain copolymer molecules, each of which includes one or more soft segments and one or more uniform hard segments (e.g., polyamide segments that do not vary in length from molecule to molecule, among others).

7 Claims, 1 Drawing Sheet

OTHER PUBLICATIONS

Osamu Soga et al., " Thermosensitive and biodegradable polymeric micelles for paclitaxel delivery," *Journal of Controlled Release*, vol. 103, 2005, pp. 341-353.

Fabiana Quaglia et al., "New segmented copolymers containing poly(ε-caprolactone) and etheramide segments for the controlled release of bioactive compounds," *Journal of Controlled Release*, vol. 83, 2002, pp. 263-271.

Ron M. Versteegen et al., "Synthesis and Characterization of Segmented Copoly(etherurea)s with Uniform Hard Segments," *Macromolecules*, vol. 38, 2005, pp. 3176-3184.

Guido Kickelbick, "Concepts for the incorporation of inorganic building blocks into organic polymers on a nanoscale," *Progress in Polymer Science*, vol. 28, 2003, pp. 83-114.

Pei-Chun Chiang et al., "Effects of titania content and plasma treatment on the interfacial adhesion mechanism of nano titania-hybridized polyimide and copper system," *Polymer*, vol. 45, 2004, pp. 4465-4472.

Ruth Duncan, "Polymer conjugates for tumour targeting and intracytoplasmic delivery. The EPR effect as a common gateway?" *PSTT*, vol. 2, 1999, pp. 441-449.

Ruth Duncan, "Polymer-drug conjugates, PDEPT and PELT: basic principles for design and transfer from the laboratory to clinic," *Journal of Controlled Release*, vol. 74, 2001, pp. 135-146.

Ruth Duncan, "The Dawning Era of Polymer Therapeutics," Nature Reviews, vol. 2, May 2003, pp. 347-360.

Chun Li, "Poly(L-glutamic acid)-anticancer drug conjugates," *Advanced Drug Delivery Reviews*, vol. 54, 2002, pp. 695-713.

Afsaneh Lavasanifar et al., "Poly(ethylene oxide)-*block*-poly(L-amino acid) micelles for drug delivery," *Advanced Drug Delivery Reviews*, vol. 54, 2002, pp. 169-190.

Yoshinori Kakizawa et al., "Block copolymer micelles for delivery of gene and related compounds," *Advanced Drug Delivery Reviews*, vol. 54, 2002, pp. 203-222.

Sweta Modi et al., "Polymer-drug conjugates: Recent development for anticancer drugs," *CRIPS*, vol. 5, 2004, pp. 2-8.

Ramesh Panchagnula, "Pharmaceutical aspects of paclitaxel," *International Journal of Pharmaceutics*, vol. 172, 1998, pp. 1-15.

A.A. Deschamps et al., "Poly(ether ester amide)s for tissue engineering," *Biomaterials*, vol. 24, 2003, pp. 263-2652.

X.Y. Xiong et al., "Release kinetics of hydrophobic and hydrophilic model drugs from pluronic F127/poly(lactic acid) nanoparticles," *Journal of Controlled Release*, vol. 103, 2005, pp. 73-82.

Chau-Hui Wang et al., "Enzymatic degradation of PLLA-PEOz-PLLA triblock copolymers," *Biomaterials*, vol. 26, 2005, pp. 2803-2811.

Mingjun Liu et al., "Designing dendrimers for drug delivery," *PSTT*, vol. 2, 1999, pp. 393-401.

R.A. Zoppi et al., "Hybrid films of poly(ethylene oxide-*b*-amide-6) containing sol-gel silicon or titanium oxide as inorganic fillers: effect or morphology and mechanical properties on gas permeability," *Polymer*, vol. 41, 2000, pp. 5461-5470.

V. Münchow et al., "Poly[(oligothylene glycol) dihydroxytitanate] as organic-inorganic polymer-electrolytes," Electrochimica Acta, vol. 45, 2000, pp. 1211-1221.

Carlos Elvira et al., "Covalent Polymer-Drug Conjugates," *Molecules*, vol. 10, 2005, pp. 114-125.

Reinoud J. Gaymans et al., "Nano-reinforcement by crystallization in blockcopolymers," DPI projects 140, 137, 312, 313, 5 pp., 2004.

\* cited by examiner

MEDICAL DEVICES FOR THERAPEUTIC AGENT DELIVERY WITH POLYMERIC REGIONS THAT CONTAIN COPOLYMERS HAVING BOTH SOFT SEGMENTS AND UNIFORM LENGTH HARD SEGMENTS

FIELD OF THE INVENTION

The present invention relates generally to medical devices, and more particularly to therapeutic-agent-releasing medical devices which contain polymeric regions.

BACKGROUND OF THE INVENTION

Controlled release of therapeutic agents by means of polymeric materials has existed in various forms for many years. For example, numerous polymer-based medical devices have been developed for the delivery of therapeutic agents to the body. Examples include drug eluting coronary stents, which are commercially available from Boston Scientific Corp. (TAXUS), Johnson & Johnson (CYPHER), and others.

There is an ongoing need for high performance polymeric materials that can be used in medical devices, including those which regulate the release therapeutic agents. Among various attributes of the polymer or polymers making up such materials, the molecular weight, architecture (e.g., linear, cyclic, branched), monomeric constituents, as well as the proportion and distribution of the monomeric constituents (where copolymers are employed) will commonly influence one or more characteristics of the materials, including the biocompatibility, mechanical characteristics, processability, and therapeutic agent release profile.

SUMMARY OF THE INVENTION

According to an aspect of the present invention, implantable or insertable medical devices are provided, which contain polymeric regions that regulate the release of therapeutic agents. These polymeric regions, in turn, contain one or more types of polymers, at least one of which is a copolymer that contains at least one soft segment and at least one uniform length hard segment.

Advantages of the present invention are that polymeric regions may be formed, which have one or more enhanced characteristics selected from the following: therapeutic agent storage and release, tensile strength, modulus, durability, biocompatibility, biostability and processability, among others.

These and other aspects, embodiments and advantages of the present invention will become readily apparent to those of ordinary skill in the art upon review of the Detailed Description and Claims to follow.

DETAILED DESCRIPTION

A more complete understanding of the present invention is available by reference to the following detailed description of various aspects and embodiments of the invention. The detailed description of the invention which follows is intended to illustrate but not limit the invention.

As noted above, the invention generally relates to implantable or insertable medical devices, which contain polymeric regions that regulate the release of therapeutic agents. These polymeric regions, in turn, contain one or more types of polymers, at least one of which is a copolymer that contains at least one soft segment and at least one uniform length hard segment.

Implantable and insertable medical devices benefiting from the various aspects and embodiments of the present invention are numerous and may be selected, for example, from the following: catheters (e.g., renal or vascular catheters such as balloon catheters), balloons, guide wires, filters (e.g., vena cava filters), stents (including coronary vascular stents, peripheral vascular stents, cerebral, urethral, ureteral, biliary, tracheal, gastrointestinal and esophageal stents), stent grafts, vascular grafts, vascular access ports, embolization devices including cerebral aneurysm filler coils (such as Guglilmi detachable coils and various other metal coils), myocardial plugs, septal defect closure devices, patches, pacemakers and pacemaker leads, defibrillation leads and coils, left ventricular assist hearts and pumps, total artificial hearts, heart valves, vascular valves, tissue engineering scaffolds for in vivo tissue regeneration, biopsy devices, as well as many other devices that are implanted or inserted into the body and from which therapeutic agent is released.

The medical devices of the present invention include medical devices that are used for diagnosis, for systemic treatment, or for the localized treatment of any tissue or organ, for example, the following: tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, liver and pancreas, skeletal muscle, smooth muscle, breast, dermal tissue, and cartilage. As used herein, "treatment" refers to the prevention of a disease or condition, the reduction or elimination of signs or symptoms associated with a disease or condition, or the substantial or complete elimination of a disease or condition. Typical subjects (also referred to as "patients") are vertebrate subjects, more typically mammalian subjects, and even more typically human subjects.

In various embodiments of the invention, devices are adapted for delivery of therapeutic agents into tissue. For example, the devices can be used to deliver therapeutic agents into various tissue surfaces, including the exterior walls of tissue such as the wall of the heart and the bladder, among others. Therapeutic agent can also be delivered to lumen walls, for example, those corresponding to the following: lumens of the cardiovascular system such as the heart, arteries (e.g., aorta, coronary, femoral, ilial, carotid and vertebrobasilar arteries, etc.) and veins, lumens of the genitourinary system such as the urethra (including prostatic urethra), bladder, ureters, vagina, uterus, spermatic and fallopian tubes, the nasolacrimal duct, the eustachian tube, lumens of the respiratory tract, such as the trachea, bronchi, nasal passages and sinuses, lumens of the gastrointestinal tract such as the esophagus, gut, duodenum, small intestine, large intestine, colon, biliary and pancreatic duct systems, lumens of the lymphatic system, the major body cavities (peritoneal, pleural, pericardial), and so forth.

"Therapeutic agents," "drugs," "bioactive agents," "pharmaceuticals," "pharmaceutically active agents", and other related terms may be used interchangeably herein and include genetic and non-genetic therapeutic agents. Therapeutic agents may be used singly or in combination. A wide range of therapeutic agent loadings can be used in conjunction with the devices of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

Therapeutic agents may be selected, for example, from the following: adrenergic agents, adrenocortical steroids, adrenocortical suppressants, alcohol deterrents, aldosterone antagonists, amino acids and proteins, ammonia detoxicants, anabolic agents, analeptic agents, analgesic agents, androgenic agents, anesthetic agents, anorectic compounds, anorexic agents, antagonists, anterior pituitary activators and suppressants, anthelmintic agents, anti-adrenergic agents, anti-allergic agents, anti-amebic agents, anti-androgen agents, anti-anemic agents, anti-anginal agents, anti-anxiety agents, anti-arthritic agents, anti-asthmatic agents, anti-atherosclerotic agents, antibacterial agents, anticholelithic agents, anticholelithogenic agents, anticholinergic agents, anticoagulants, anticoccidal agents, anticonvulsants, antidepressants, antidiabetic agents, antidiuretics, antidotes, antidyskinetics agents, anti-emetic agents, anti-epileptic agents, anti-estrogen agents, antifibrinolytic agents, antifungal agents, antiglaucoma agents, antihemophilic agents, antihemophilic Factor, antihemorrhagic agents, antihistaminic agents, antihyperlipidemic agents, antihyperlipoproteinemic agents, antihypertensives, antihypotensives, anti-infective agents, anti-inflammatory agents, antikeratinizing agents, antimicrobial agents, antimigraine agents, antimitotic agents, antimycotic agents, antineoplastic agents, anti-cancer supplementary potentiating agents, antineutropenic agents, antiobsessional agents, antiparasitic agents, antiparkinsonian drugs, antipneumocystic agents, antiproliferative agents, antiprostatic hypertrophy drugs, antiprotozoal agents, antipruritics, antipsoriatic agents, antipsychotics, antirheumatic agents, antischistosomal agents, antiseborrheic agents, antispasmodic agents, antithrombotic agents, antitussive agents, anti-ulcerative agents, anti-urolithic agents, antiviral agents, benign prostatic hyperplasia therapy agents, blood glucose regulators, bone resorption inhibitors, bronchodilators, carbonic anhydrase inhibitors, cardiac depressants, cardioprotectants, cardiotonic agents, cardiovascular agents, choleretic agents, cholinergic agents, cholinergic agonists, cholinesterase deactivators, coccidiostat agents, cognition adjuvants and cognition enhancers, depressants, diagnostic aids, diuretics, dopaminergic agents, ectoparasiticides, emetic agents, enzyme inhibitors, estrogens, fibrinolytic agents, free oxygen radical scavengers, gastrointestinal motility agents, glucocorticoids, gonad-stimulating principles, hemostatic agents, histamine H2 receptor antagonists, hormones, hypocholesterolemic agents, hypoglycemic agents, hypolipidemic agents, hypotensive agents, HMGCoA reductase inhibitors, immunizing agents, immunomodulators, immunoregulators, immune response modifiers, immunostimulants, immunosuppressants, impotence therapy adjuncts, keratolytic agents, LHRH agonists, luteolysin agents, mucolytics, mucosal protective agents, mydriatic agents, nasal decongestants, neuroleptic agents, neuromuscular blocking agents, neuroprotective agents, NMDA antagonists, non-hormonal sterol derivatives, oxytocic agents, plasminogen activators, platelet activating factor antagonists, platelet aggregation inhibitors, post-stroke and post-head trauma treatments, progestins, prostaglandins, prostate growth inhibitors, prothyrotropin agents, psychotropic agents, radioactive agents, repartitioning agents, scabicides, sclerosing agents, sedatives, sedative-hypnotic agents, selective adenosine A1 antagonists, serotonin antagonists, serotonin inhibitors, serotonin receptor antagonists, steroids, stimulants, thyroid hormones, thyroid inhibitors, thyromimetic agents, tranquilizers, unstable angina agents, uricosuric agents, vasoconstrictors, vasodilators, vulnerary agents, wound healing agents, xanthine oxidase inhibitors, and the like.

Numerous additional therapeutic agents useful for the practice of the present invention may be selected from those described in paragraphs [040] to [0046] of commonly assigned U.S. Patent Application Pub. No. 2003/0236514, the entire disclosure of which is hereby incorporated by reference.

Some specific beneficial agents include anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

More specific examples of therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein, resiquimod, imiquimod (as well as other imidazoquinoline immune response modifiers), human apolioproteins (e.g., AI, AII, AIII, AIV, AV, etc.), vascular endothelial growth factors (e.g., VEGF-2), as well a derivatives of the forgoing, among many others.

As noted above, the medical devices of the present invention utilize polymeric regions that contain copolymers, which in turn contain at least one soft segment and at least one uniform length hard segment. In certain embodiments, 25 wt % to 50 wt % to 75 wt % to 90 wt % to 95 wt % or more of the copolymers within the polymeric region may have uniform length hard segments.

By a "polymeric" region is meant a region that contains polymers, commonly at least 50 wt %, 75 wt %, 90 wt %, 95 wt % or even more, polymers.

As used herein, "polymers" are molecules that contain multiple copies of the same or differing constitutional units, commonly referred to as monomers, and typically containing from 5 to 10 to 25 to 50 to 100 to 250 to 500 to 1000 or more constitutional units. Hence, as used herein, "polymers" include oligomers having as few as two constitutional units. As used herein, "homopolymers" are polymers that contain multiple copies of a single constitutional unit. "Copolymers" are polymers that contain multiple copies of at least two dissimilar constitutional units. As used herein, a "polymer segment" is a grouping of constitutional units (e.g., containing from 2 to 3 to 4 to 5 to 10 to 25 to 50 to 100 to 250 to 500 to 1000 or more constitutional units), which forms a portion of a polymer. Depending on the number and nature of the segments making them up, the polymers for use in the present invention may have a variety of architectures, including cyclic, linear and branched architectures. Branched architectures include star-shaped architectures (e.g., architectures in which three or more linear segments emanate from a single branch point), comb architectures (e.g., architectures having a main chain and a plurality of side chains) and dendritic architectures (e.g., arborescent and hyperbranched polymers), among others. The polymers may contain, for example, homopolymer segments, which contain a single constitutional unit, and/or copolymer segments, which contain at least two dissimilar constitutional units, which dissimilar units may be present in any of a variety of distributions, including random, statistical, gradient, and periodic (e.g., alternating) distributions. As used herein, "block copolymers" are polymers containing two or more differing polymer segments, for example, selected from homopolymer segments, random copolymer segments and periodic copolymer segments.

Specific examples of copolymers which may contain at least one soft segment and at least one uniform length hard segment include (a) poly(ether amide) block copolymers, which contain at least one polyether segment and at least one uniform length polyamide segment and (b) poly(ether urea) block copolymers, which contain at least one polyether segment and at least one uniform length polyurea segment.

As used herein, "uniform polyamide segments" or "uniform length polyamide segments" are polymer segments (which as noted above may contain as few as two constitutional units) that contain one or more amide linkages (—CO—NH—) and which are of the same length from molecule to molecule. It is noted that this is not typical of polymers, including block copolymers, whose polymeric segments ordinarily differ somewhat in length from molecule to molecule. In certain embodiments of the invention, 25 wt % to 50 wt % to 75 wt % to 90 wt % to 95 wt % or more of the poly(ether amide) molecules within a polymeric region have uniform polyamide segments.

As used herein, "uniform polyurea segments" or "uniform length polyurea segments" are polymer segments, which contain one or more carbonyldiimino linkages (—NH—CO—NH—), also sometimes referred to as ureylene or urylene linkages, and which are of the same length from molecule to molecule. In certain embodiments of the invention, 25 wt % to 50 wt % to 75 wt % to 90 wt % to 95 wt % or more of the poly(ether urea) molecules within a polymeric region have uniform polyurea segments.

The polyether segments within such poly(ether amides) and poly(ether ureas) include low $T_g$ segments (also referred to herein as "soft segments" because they are soft, and frequently elastomeric, at ambient temperature), whereas the polyamide segments and the polyurea segments include high $T_g$ segments (also referred to herein as "hard segments," because they are hard, and frequently crystalline, at ambient temperature). "Low $T_g$ polymer segments" are polymer segments that display a $T_g$ that is below ambient temperature, more typically below 20° C., below 0° C., below −25° C., or even below −50° C. Conversely, elevated or "high $T_g$ polymer segments" are polymer segments that display a glass transition temperature that is above ambient temperature, more typically above 50° C., above 75° C., or even above 100° C. In some instances, the $T_g$ of the hard segments may be greater than the melting point of the material and thus not observed. $T_g$ can be measured by any of a number of techniques including differential scanning calorimetry (DSC), dynamic mechanical analysis (DMA), or dielectric analysis (DEA). "Ambient temperature" is typically 25° C.-45° C., more typically body temperature (e.g., 35° C.-40° C.).

The soft segments (S) and hard segments (H) may be organized within the block copolymers of the present invention in a variety of ways, including: (a) block copolymers having alternating chains of the type $(HS)_m$, $S(HS)_m$ or $H(SH)_m$ where m is a positive whole number of 1 or more, (b) block copolymers having multi-arm geometries such as $X(SH)_n$ or $X(HS)_n$, where n is a positive whole number of 2 or more, and X is a hub species (e.g., an initiator molecule residue, a residue of a molecule to which preformed polymer chains are attached, etc.), and (c) comb block copolymers such as those having a S chain backbone and multiple H side chains, or those having an H chain backbone and multiple S side chains.

Examples of polyether segments which may be employed in the poly(ether amides) and poly(ether ureas) of the invention include poly(alkylene oxide) segments, aromatic polyether segments and their derivatives, which may be provided, for example, in the form of homopolymer segments and/or copolymer segments. A few specific examples of poly(alkylene oxides) are those of the formulas, HO—[$R_1$—O—]$_n$—H, HO—[$R_2$—O—$R_3$—O]$_n$—H, and HO—[$R_4$—O]$_n$—[$R_5$—O]$_m$—H, where $R_1$, $R_2$, $R_3$, $R_4$ and $R_5$ may be selected from linear, branched and cyclic alkyl groups, aromatic groups and alky-aromatic groups having from 1 to 10 carbon atoms (more typically linear or branched alkyl groups having from 1 to 6 carbons) and where n and m are integers of 2 or more, for example, ranging from 2 to 5 to 10 to 25 to 50 to 100 to 250 to 500 to 1000 or more. Polyethers may be formed, for example, from ring opening addition polymerization of cyclic ethers, among other techniques.

More specific examples include (a) polyethylene oxide, where $R_1$ is dimethylene (i.e., HO[—$CH_2$—$CH_2$—O—]$_n$H), which is also commonly referred to as polyethylene glycol (PEG); (b) poly(trimethylene oxide), where $R_1$=trimethylene (i.e., HO[—$CH_2$—$CH_2$—$CH_2$—O—]$_n$H); (c) poly(propylene oxide), where $R_1$=methyl substituted dimethylene (i.e., HO[—$CH_2$—$CH_2(CH_3)$—O—]$_n$H, also referred to as poly (propylene glycol); (d) polytetramethylene oxide (PTMO), where $R_1$=tetramethylene (i.e., HO[—$(CH_2)_4$—O—]$_n$H, which is also referred to as polytetramethylene glycol and poly(tetrahydrofuran); (e) methyl-substituted polytetramethylene oxide (mPTMO), where $R_1$=methyl substituted tetramethylene

(f) poly(phenylene oxide) and (g) combinations and derivatives of the same. Some examples of PTMO derivatives include where n and m are integers.

As noted above, in addition to polyether segments, the poly(ether amide) copolymers used in the polymeric regions of the present invention also comprise uniform polyamide segments. In certain embodiments, these uniform polyamide segments are short in length, for example, containing from 1 to 2 to 5 to 10 to 25 amide linkages. Moreover, in certain embodiments, the uniform polyamide segments may contain one or more aromatic structures (e.g., a benzene ring structure, among many others), which are believed to assist with self assembly of distinct phase domains.

Some specific examples of short uniform aromatic polyamides that may be incorporated into poly(ether amides) in conjunction with the present invention include uniform aromatic poly(ester amides) such as the following:

(referred to as TΦT dimethyl ester),

(referred to as TmdaT dimethyl ester), (referred to as TtolT dimethyl ester), (referred to as TmΦT dimethyl ester), and (referred to as T6T6T dimethyl ester).

An example of a reaction of PTMO with TΦT dimethyl to form a poly(ether amide) follows (taken from M. C. E. J. Niesten et al., "Synthesis and properties of segmented copolymers having aramid units of uniform length," *Polymer* 41 (2000) 8487-8500):

where NMP is N-methyl-2-pyrrolidone, P is pressure, T is temperature, and n and p are integers. Another example is the reaction of PTMO/DMT with TΦT dimethyl ester, which yields the following copolymer:

| T | Φ | T | PTMO | T | PTMO | where n, m and p are integers.

Figure 1:
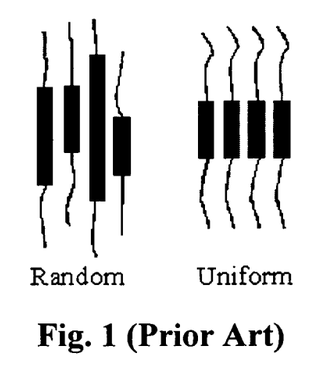
FIG. 1 is a schematic illustration of two block copolymers, one having hard segments of uniform length and the other having hard segments of random length.
Figure 2:
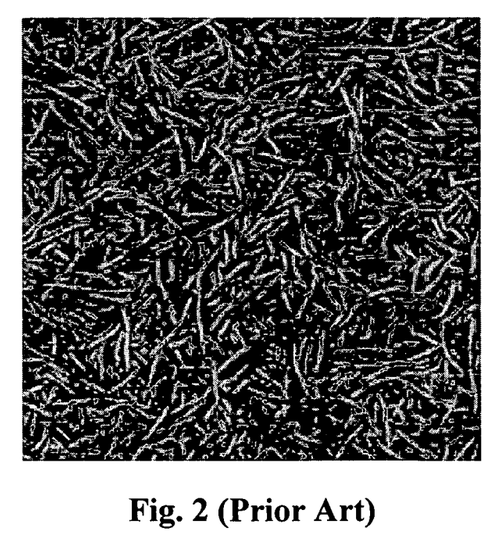
FIG. 2 is an atomic force micrograph of a copolymer like that illustrated schematically in FIG. 1.

Such segmented block copolymers are typically two-phase materials consisting of an amorphous soft phase with a low glass transition temperature ($T_g$) and a dispersed, hard, crystalline phase with a high melting temperature ($T_m$). Without wishing to be bound by theory of operation, the polyamide segments, which are uniform in length and are capable of forming hydrogen bonds, provide neater crystal packing as compared to segments with a random length distribution as illustrated schematically in FIG. 1. The crystallized polyamide segments have been observed to stack into ribbon-like crystallites. An atomic force micrograph of such a polymer is illustrated in FIG. 2. As all of the polyamide segments have the same length, crystallization is believed to occur over the full length of the amide segment and the crystallinity is therefore high. Such block copolymers have high melting temperatures, even with relatively short polyamide segments, and the dimensional stability of the polymer is good.

For further information on poly(ether amides) having structures such as those illustrated above, see, e.g., B. B. Sauer et al., "Crystalline Morphologies in Segmented Copolymers with Hard Segments of Uniform Length," *J. Polym. Sci. B: Polym. Phys.* 2004, 42(9), 1783-1792; M. C. E. J. Niesten et al., "Tensile and elastic properties of segmented copolyetheresteramides with uniform aramid units," *Polymer* 42 (2001) 6199-6207; M. C. E. J. Niesten et al., "Segmented copolyetheresteraramids with extended poly(tetramethyleneoxide) segments," *Polymer* 42 (2001) 1461-1469; M. C. E. J. Niesten et al., "Influence of type of uniform aromatic amide units on segmented copolyetheresteramides, *Polymer* 42 (2001) 931-939; J. Krijgsman et al., "Synthesis and properties of thermoplastic elastomers based on PTMO and tetra-amide," *Polymer* 44 (2003) 7573-7588; M. C. E. J. Niesten et al., "Synthesis and properties of segmented copolymers having aramid units of uniform length," *Polymer* 41 (2000) 8487-8500; Martijn van der Schuur et al., "Structure-property relations of segmented block copolymers with liquid-liquid demixed morphologies," *Polymer* 46 (2005) 3616-3627; M. R. Hibbs et al., "Poly(ethylene terephthalate) Modified with Aromatic Bisester Diamides: Thermal and Oxygen Barrier Properties," *Journal of Polymer Science: Part A: Polymer Chemistry*, Vol. 42, 1668-1681 (2004).

Other examples of polyamide segments include polyamide segments of the formula —[$R_6$—NH—CO]$_m$—, —[NH—$R_7$—NH—CO—$R_8$—CO]$_m$ and —[$R_9$—NH—CO]$_m$—[$R_{10}$—NH—CO]$_m$— where $R_6$, $R_7$, $R_8$, $R_9$ and $R_{10}$ may be selected from linear, branched and cyclic alkyl groups, aromatic groups and alky-aromatic groups of 1 to 20 carbon atoms (more typically linear or branched alkyl groups having from 1 to 15 carbons, such as methyl, ethyl, propyl, isopropyl, and so forth) and where m and n are integers, for example, ranging from 3 to 5 to 10 to 25 or more. Specific examples include nylons, such as nylon 6 (polycaprolactam), nylon 4/6, nylon 6/6, nylon 6/10, nylon 6/12, nylon 11 and nylon 12, and poly(amino acids) (PAAs) such as poly(L-glutamic acid)

poly(L-lysine)

and mixed peptides.

A few examples of amino acid sequences which may be employed include those which self assemble into fibrils. A few examples of structures that have been reported as self-assembling into fibrils and ribbons including NFGAIL, FGAIL, FGAILSS, TNVGSNTY, QRLANFLVH, KLVF-FAE, GNNQQNY, FLVHS, NFLVH, ATQRLANFLVHSS. Because these segments contain aromatic structures (e.g., F=phenylalanine, Y=tyrosine, W=tryptophan), π-stacking has been proposed as possibly playing a role in the self-assembly process. For further information, see, e.g., E. Gazit, "A possible role for π-stacking in the self-assembly of amyloid fibrils," *The FASEB Journal*, Vol. 16 January 2002, 77-83 and Y. Mazor et al., "Identification and Characterization of a Novel Molecular-recognition and Self-assembly Domain within the Islet Amyloid Polypeptide," *J. Mol. Biol.* (2002) 322, 1013-1024; "Peptides self-assemble into higher order morphological structures via helical ribbon intermediates," *Heart Cut*, May 13, 2002.

Other examples of uniform polyamide segments, which are not linear, are polyamide dendrimer segments. Because dendrimers are grown generation by generation, reaction within a given generation ceases once all of the available reaction sites have reacted, thereby affording the opportunity to provide uniform segments. One example of a poly(ether amide) with uniform polyamide dendrimer segments, specifically, a polylysine-PEG-polylysine triblock copolymer, is illustrated below:

See e.g., F. Aulenta et al., "Dendrimers: a new class of nanoscopic containers and delivery devices," European Polymer Journal 39 (2003) 1741-1771.

Other examples of polyamide dendrimer segments, which may serve as uniform segments within the poly(ether amides) of the invention, include those poly(ether amides) that contain (a) one or more polyether segments and (b) one or more amine terminated uniform PMAM segments and/or one or more carboxyl terminated uniform PMAM segments. See, e.g., Id. at 1748 for examples of such segments.

Yet another example of a poly(ether amide) for use in the present invention is the following poly(ether aromatic amide):

where R includes one or more polyether segments and an appropriate linkage for covalently coupling the polyether to the aromatic polyamide structure.

Still other poly(ether amides) for use in the present invention are biodegradable. One specific example of such as structure is where x and y are integers and where

See, e.g., N. Kumar, "Biodegradable block copolymers," *Advanced Drug Delivery Reviews* 53 (2001) 23-44

An example of another biodegradable polyamide block which may be employed as a uniform polyamide segment is poly(N-(2-hydroxypropyl)methacrylamide lactate) (pHPMAmDL). pHPMAmDL-b-PEG polymers, although without uniform polyamide segments, are described for example, in O. Soga et al., "Thermosensitive and biodegradable polymeric micelles for paclitaxel delivery," Journal of Controlled Release 103(2005) 341-353.

Other examples of poly(ether amides), specifically, poly (ether-ester-amides), which include uniform-length polyether (trioxyethylene and pentaoxyethylene) soft segments, polyester (polycaprolactone) soft segments, and uniform-length polyamide (Gly-Phe) hard segments, are described in F. Quaglia et al., "New segmented copolymers containing poly(∈-caprolactone) and etheramide segments for the controlled release of bioactive compounds," *Journal of Controlled Release*, 83 (2002) 263-271.

As noted above, in addition to polyether segments such as those described above, among others, the poly(ether urea) copolymers used in the polymeric regions of the present invention also comprise uniform polyurea segments. Several specific examples of poly(ether urea) copolymers having uniform polyurea segments are set forth, for instance, in R. M. Versteegen et al., "Synthesis and Characterization of Segmented Copoly(ether urea)s with Uniform Hard Segments," *Macromolecules* 2005, 38, 3176-3184, which describes poly (ether ureas) having one or more poly(tetrahydrofuran) soft segments and one or more uniform polyurea segments. Specific examples are as follows:

(c)

(d)

wherein pTHF designates a poly(tetrahydrofuran) segment, n is an integer (i.e., 1,2,3, etc.), R is —CH$_2$)$_m$— and m=2 to 6.

If desired, the polymers making up the polymeric regions of the present invention may be crosslinked with various agents to achieved desired properties (e.g., to reduce solubility, etc.).

In addition to copolymers that contain at least one soft segment and at least one uniform length hard segment, the polymeric regions of the invention may further contain other polymers, for example, blended with the same.

In certain aspects of the invention, the polymeric regions contain polymer molecules that comprise covalently linked metallic or semi-metallic elements. For example, in some embodiments, the metallic or semi-metallic elements may be covalently linked to the above described block copolymers, including, for example, poly(ether amide) block copolymers that contain at least one polyether segment and at least one uniform length polyamide segment, and poly(ether urea) block copolymers that contain at least one polyether segment and at least one uniform length polyurea segment, among others. In other embodiments, the metallic or semi-metallic elements may be covalently linked to other polymer molecules, for example, polyether molecules, polyamide molecules, polyurea molecules, poly(ether amide) block copolymers that do not contain uniform length polyamide segments, poly(ether urea) block copolymers that do not contain uniform length polyurea segments, and so forth.

Polymer molecules that comprise covalently linked metallic or semi-metallic elements may be integrated into the polymeric regions of the present invention using sol-gel processes.

In a typical sol-gel process, precursor materials, typically inorganic metallic and semi-metallic salts, metallic and semi-metallic complexes/chelates, metallic and semi-metallic hydroxides, or organometallic and organo-semi-metallic compounds such as metal alkoxides and alkoxysilanes, are subjected to hydrolysis and condensation (also referred to as polymerization) reactions, thereby forming a "sol". For example, an alkoxide of choice (such as a methoxide, ethoxide, isopropoxide, tert-butoxide, etc.) of a semi-metal or metal of choice (such as silicon, zirconium, titanium, aluminum, tin, hafnium, tantalum, molybdenum, tungsten, rhenium, iridium, etc.) may be dissolved in a suitable solvent, for example, in one or basic aqueous solution (which aqueous solution can further contain organic solvent species such as alcohols) is added, causing hydrolysis and condensation to occur.

As can be seen from the simplified scheme below (from G. Kickelbick, "Concepts for the incorporation of inorganic building blocks into organic polymers on a nanoscale" *Prog. Polym. Sci.*, 28 (2003) 83-114, the entire disclosure of which is incorporated herein by reference), the reaction is basically a ceramic network forming process in which the metal/semi-metal atoms (designated generally herein as M) within the ceramic phases are linked to one another via covalent linkages, such as M-O-M linkages, although other interactions are also commonly present including, for example, hydrogen bonding due to the presence of hydroxyl groups such as residual M-OH groups within the network:

Hydrolysis:

Condensation:

2 M(OR)$_{n-m}$(OH)$_m$ ⟶

M = Si, Ti, Zr, Sn, Al, ...
R = Me, Et, $^i$Pr, $^n$Pr, $^n$Bu, $^s$Bu, ...

Further processing of the sol enables solid materials to be made in a variety of different forms. For instance, thin films can be produced on a substrate by spray coating, coating with an applicator (e.g., by roller or brush), spin-coating, dip-coating, and so forth, of the sol onto the substrate, whereby a "wet gel" is formed. Where dip coating is employed, the rate of withdrawal from the sol can be varied to influence the properties of the film. Monolithic wet gels can be formed, for example, by placing the sol into or onto a mold or another form (e.g., a sheet) from which the dried gel can be released. The wet gel is then dried. If the solvent in the wet gel is removed under supercritical conditions, a material commonly called an "aerogel" is obtained. If the gel is dried via freeze drying (lyophilization), the resulting material is commonly referred to as a "cryogel." Drying at ambient temperature and ambient pressure leads to what is commonly referred to as a "xerogel." Other drying possibilities are available including elevated temperature drying (e.g., in an oven), vacuum drying (e.g., at ambient or elevated temperatures), and so forth.

Analogously, in some embodiments of the invention, polymers may be provided with metallic- or semi-metallic-element-containing groups that are capable of participation in hydrolysis/condensation reactions.

In certain of these embodiments, hybrid monomer species may be incorporated into polymers via suitable polymerization techniques, typically in the presence of one or more comonomers. For example, the hybrid monomer species may have additional groups, such as -M(OR)$_m$ groups (where M is a metal or semi-metal, m is an integer whose value will depend on the valency of M, typically ranging from 3 to 6, and the various R groups, which may be the same or different, are linear, branched or cyclic alkyl groups, aromatic groups or alky-aromatic groups of 1 to 10 carbon atoms, and preferably linear or branched alkyl groups having from 1 to 6 carbons, e.g., methyl, ethyl, propyl, isopropyl, and so forth). The inorganic groups incorporated into the resulting polymer are then available to participate in the hydrolysis/condensation reactions that are associated with sol-gel processing (optionally, in conjunction with another organometallic or organo-semi-metallic compound, such as M(OR)$_{m+1}$, where M, m, and R are defined above), thereby forming a ceramic network that is covalently linked to the polymeric phase.

In certain other of these embodiments, preexisting polymers are provided with inorganic groups that are capable of participating in hydrolysis/condensation. For example, using appropriate linking chemistry, a wide variety of polymers, including the polymers described above, can be provided with groups for participation in sol-gel processing. Specific examples of polymers that are readily modified with organometallic or organo-semi-metallic groups for participation in sol gel processing are polymers that have hydroxyl groups, including polyethers and polyesters. A few specific examples of hydroxyl-bearing polymers follow: polyethers such as those of the formulas, HO—[R$_1$—O—]$_n$—H, HO—[R$_2$—O—R$_3$—O]$_n$—H, and HO—[R$_4$—O]$_n$—[R$_5$—O]$_m$—H, set forth above, (b) polyesters, such as poly(ethylene terephthalate), (c) polyester/polyether block copolymers, e.g., HO—[CO—PEST—CO—PETH—O—]H, where PEST designates a polyester block and PETH designates a polyether block, e.g., HYTREL poly(dimethyl terephthalate)-block-poly(tetramethylene ether glycol) copolymers available from DuPont and ARNITEL poly(butylene terephthalate)-block-poly(tetramethylene oxide) copolymers available from DSM Engineering Plastics, (d) polyether/polyamide block copolymers, e.g., HO—[CO—PA—CO—O—PE—O—]H, where PE designates a polyether block and PA designates a polyamide block, such as poly(tetramethylene oxide)-polyamide 12 block copolymer (PEBAX) available from Elf Atochem.

Suitable members of the above hydroxyl-bearing polymers (as well as numerous other polymers having hydroxyl groups or polymer that are modified to include hydroxyl groups) may be modified to contain groups which are capable of participation in hydrolysis/condensation, for example, by reaction with an appropriate species such as M(OR)$_m$(R—N=C=O), where M, m and R are previously defined, to provide the polymer with one or alkoxy groups -M(OR)$_m$.

For example, a polyether of the formula HO—[R$_1$—O—]$_n$H, where R$_1$ is alkyl (e.g., PEO, PPO, PTMEG, etc.), may be reacted with M(OR)$_m$(R—N=C=O) to produce (RO)$_m$M-R—NH—CO—O—[R$_1$—O—]$_n$H or (RO)$_m$M-R—NH—CO—O—[R$_1$—O—]$_n$O—CO—NH—R-M(OR)$_m$. The various M(OR)$_m$ groups are then available for hydrolysis/condensation as described above, optionally, in the presence of an inorganic species such as M(OR)$_{m+1}$.

In some embodiments, the resulting polymer (e.g., a modified polymer having -M(OR)$_m$ groups) may be subjected to an additional polymerization step. As a specific example, a polyether (e.g., the above polyether of the formula (RO)$_m$M-R—NH—CO—O—[R—O—]$_n$H) may be used for block copolymerization with a polyamide forming monomer to form a polyether-polyamide block copolymer, which has groups for participation in the sol gel reaction. This is in contrast with the direct modification of a polyether-polyamide block copolymer to provide -M(OR)$_m$ groups as described above.

In a specific example, a hybrid poly(ether amide) triblock copolymer having a uniform length polyamide center segment (e.g., biester diamides such as TΦT, other polyamides such as T6T6T, etc.) and polyether end segments (e.g., PEO, PTMO etc.) may be provided, in which the polyether end segments are functionalized with metal alkoxide species (e.g., titanium, zirconium or silicon alkoxide groups). Upon deposition onto an underlying substrate (e.g., onto a metal such as nitinol by a process like that described above, which comprises dissolution in a suitable solvent, after which water or another aqueous solution, such as an acidic or basic aqueous solution, is added to cause hydrolysis and condensation to occur, followed by deposition of the resulting sol to form a wet gel, followed by drying), a porous layer is produced which may be optimized to regulate drug release (e.g., by adding various amounts of an optional as inorganic species such as M(OR)$_{m+1}$). In addition such layers may allow for good adhesion to underlying substrates, particularly, metallic substrates such as nitinol or stainless steel, and polyether containing substrates such as PEBAX, among others.

In certain embodiments of the invention, a hybrid film having one or more polymeric phases and one or more ceramic phases (e.g., phases comprising metal oxides and/or semi-metal oxides) may be employed to improve adhesion between the polymeric regions of the invention and underlying substrates. For example, P.-C. Chiang et al., "Effects of titania content and plasma treatment on the interfacial adhesion mechanism of nano titania-hybridized polyimide and copper system," Polymer 45 (2004) 4465-4472, reported that a hybrid polyimide/titania film (along with optional plasma treatment in the presence of Ar, Ar/N$_2$ or Ar/O$_2$) significantly increased the adhesion strength between copper and polyimide.

As previously indicated, various therapeutic agents may be used in the medical devices of the present invention. These therapeutic agents may be, for example, disposed beneath or within the polymeric regions, such that the polymeric regions regulate release of the therapeutic agents.

Where the therapeutic agent is disposed beneath the polymeric region, the polymeric region may be referred to herein as a barrier region. By "barrier region" is meant a region which is disposed between a source of therapeutic agent and a site of intended release, and which controls the rate at which therapeutic agent is released. For example, in some embodiments, the medical device consists of a barrier region that surrounds a source of therapeutic agent. In other embodiments, the barrier region is disposed over a source of therapeutic agent, which is in turn disposed over all or a portion of a medical device substrate. Where disposed beneath the polymeric region, the therapeutic agent may be in pure form or provided in conjunction with a supplemental material such as a polymeric carrier.

Where the therapeutic agent is disposed within the polymeric region, the polymeric region may be referred to herein as a carrier region. By "carrier region" is meant a polymeric release region which further comprises a therapeutic agent and from which the therapeutic agent is released. For example, in some embodiments, the carrier region constitutes the entirety of the medical device (e.g., provided in the form of a stent body). In other embodiments, the carrier region corresponds to only a portion of the device (e.g., a coating overlying a medical device substrate such as a stent body).

The therapeutic agent may be covalently linked to another species such as a polymer molecule or it may be in free form (i.e., not covalently linked to another species, although other attractive forces may be present such as Van der Waals forces, ionic forces, hydrogen bonding, coordination bonding, and ionic-coordination bonding).

For example, it is known that conjugation of antitumor agents such as paclitaxel, doxorubicin, camptothecins, and platinates to polymers including amide based block copolymers can increase drug solubility, reduce systemic toxicity and improve therapeutic index. Using paclitaxel as an exemplary therapeutic agent, this agent has been linked to (a) polyamides, including polyamino acids such as polyglutamic acid/polyglutamate, (b) polyethers such as polyethylene glycol, and (c) poly(ether amides) such as poly(glutamic acid)-poly(ethylene glycol) block copolymers, among other entities.

PEG paclitaxel is produced by Pharmacia Corporation. Information regarding formation of taxol-2'esters from PEG carboxylic acid and of bis(taxol-2'esters) from PEG diacid are described in U.S. Pat. No. 5,614,549.

U.S. Pat. No. 6,730,699, which is incorporated by reference in its entirety, describes paclitaxel conjugated to various poly(amino acids) including poly(d-glutamic acid), poly(1-glutamic acid), poly(dl-glutamic acid), poly(1-aspartic acid), poly(d-aspartic acid), poly(dl-aspartic acid), poly(1-lysine), poly(d-lysine), poly(dl-lysine), copolymers of the above listed polyamino acids with polyethylene glycol (e.g., paclitaxel-poly(1-glutamic acid)-PEO), polycaprolactone, polyglycolic acid and polylactic acid, as well as poly(2-hydroxyethyl 1-glutamine), chitosan, carboxymethyl dextran, hyaluronic acid, human serum albumin and alginic acid.

Polyglutamate paclitaxel, in which paclitaxel is linked through the hydroxyl at the 2' position to the Δ carboxylic acid of the poly-L-glutamic acid)PGA), is produced by Cell Therapeutics, Inc., Seattle, Wash., USA. (The 7 position hydroxyl is also available for esterification.) This molecule is said to be cleaved in vivo by cathepsin B to liberate diglutamyl paclitaxel. Unlike PEG-paclitaxel, where paclitaxel is bound to one or both ends of the polymer, with PGA paclitaxel, the paclitaxel is bound to the carboxyl groups along the backbone of the polymer, leading to higher paclitaxel content.

For further information, see, e.g., R. Duncan et al., "Polymer—drug conjugates, PDEPT and PELT: basic principles for design and transfer from the laboratory to clinic," Journal of Controlled Release 74 (2001) 135-146, C. Li, "Poly(L-glutamic acid)—anticancer drug conjugates," Advanced Drug Delivery Reviews 54 (2002) 695-713, and U.S. Pat. No. 5,614,549.

Using the above and other strategies, paclitaxel and other therapeutic agents may be covalently linked or otherwise associated with a variety of polymer molecules including the following: (a) poly(ether amides) including those herein described as well as other poly(ether amides), (b) poly(ether ureas) including those herein described as well as other poly (ether ureas), (c) polyethers, which may be of the same or different chemical composition from the polyether segment(s) within the herein described poly(ether amides), for example, polyethylene glycol, polypropylene glycol, PTMO, mPTMO, and so forth, (d) polyamides which may be of the same or different chemical composition from the uniform polyamide segments within the herein described poly (ether amides) and, where the polyamides are of the same composition, may be uniform polyamides of the same size as the uniform polyamide segments within the herein described poly(ether amides), for example, biester diamides such as TΦT, other polyamides such as T6T6T, polyamide dendrimers, pHPMAmDL, polyamino acids including polyglutamic acid, various nylon segments, including nylon 6, nylon 4/6, nylon 6/6, nylon 6/10, nylon 6/12, nylon 11 and nylon 12, among others, (e) polyureas which may be of the same or different chemical composition from the uniform polyurea segments within the herein described poly(ether ureas) and, where the polyureas are of the same composition, they may be uniform polyureas of the same size as the uniform polyurea segments within the herein described poly(ether ureas), and (f) other polymer molecules.

The therapeutic agent may be linked to the polymer via a biodegradable linkage to facilitate release.

As indicated above, due to the introduction of uniform hard segments, the copolymers of the present invention typically self-assemble into a phase-separated morphology, for example, with a soft, flexible phase and a hard, crystalline phase, which, for example, may provide physical crosslinks and reinforce the polymer.

Poly(ether amides) and poly(ether ureas), including many of those discussed above, among others, may be amphiphilic in nature, for example, due to the presence of (a) one or more hydrophilic polyether segments and (b) one or more hydrophobic polyamide or polyurea segments. Consequently these polymers may be suitable for the incorporation of both hydrophobic and hydrophilic drugs.

Such copolymers are also attractive for drug release due to their ability to generate hydrophobic nanodomains. The hydrophobic and hydrophilic phase domains may provide compatible regions for hydrophobic and hydrophilic drugs, respectively, and the shape and orientation of the nanodomains may be tuned to adjust water permeability and to provide paths for drug diffusion.

It is also noted that certain amphiphilic block copolymers have been reported to be capable of self-assembly into micelles, which may be released from the release regions of the invention. For example poly(alkylene oxide)-poly(L-amino acid) block copolymers have been reported to assemble into micelles with the poly(alkylene oxide) segments forming the micellar shell and the poly(L-amino acid) segments forming the micellar core. Critical micelle concentrations for block copolymers are very low—typically in the μmolar range. Also, block copolymers with biodegradable core-forming segments such as poly(L-amino acids) may undergo hydrolysis and/or enzymatic degradation, producing biocompatible monomers.

The cores of these micelles may serve as nanoreservoirs for loading and release of hydrophobic therapeutic agents that are conjugated to or complexed with the polymeric backbone of the core segments or that are physically encapsulated within the core.

For example, in some instances, therapeutic agents have been conjugated to the poly(amino acid) blocks [e.g., poly(1-lysine), poly(1-aspartic acid), poly(2-hydroxyethyl-1-aspartamide), etc. blocks] of such copolymers in order to form therapeutic agent containing micelles. Depending on the degree of hydrophilicity/hydrophobicity of the conjugated drug, there may be a need to also attach additional units (e.g., hydrophobic units) to the poly(amino acid) block in order to achieve the amphilicity required for micelle formation.

In other instances, therapeutic agents have been physically encapsulated within micelles formed using poly(alkylene oxide)-block-poly(amino acids). In some cases, a therapeutic agent is physically encapsulated using poly(ethylene oxide)-block-poly(amino acids) conjugates like those described in the prior paragraph. A strong interaction between the conjugated and physically encapsulated therapeutic agents (which are the same) is believed to improve micellar stability. In other cases, poly(ethylene oxide)-block-poly(amino acids) are used which have a strong affinity for the therapeutic agent. For example, certain poly(ethylene oxide)-block-poly(amino acids) having aromatic structures (e.g., poly(amino acids) such as poly(β-benzyl-1-aspartate), poly(β-benzyl-1-glutamate), etc.) have been used to encapsulate therapeutic agents which also have aromatic structures. A π-π interaction between the aromatic core of the micelles and the aromatic structure within the drug is believed to enhance the stability of such systems. In other examples, depending on the amino acid employed, the poly(ethylene oxide)-block-poly(amino acid) copolymer can form polyionic complexes with oppositely charged macromolecules such as DNA or peptides, leading to micellization.

Additional information regarding micelles may be found, for example, in Lavasanifar A. et al., "Poly(ethylene oxide)-block-poly(1-amino acid) micelles for drug delivery," *Advanced Drug Delivery Reviews,* 54 (2002), 169-190; and Kakizawa Y. et al., "Block copolymer micelles for delivery of gene and related compounds," *Advanced Drug Delivery Reviews,* 54 (2002), 203-222.

Polymeric regions for use in the various aspects and embodiments of the present invention may be provided in a variety of forms, including layers that are formed over all or only a portion of an underlying medical device substrate, bulk device regions that do not require an underlying substrate such as scaffolds and fibers, and so forth. Layers can be provided over an underlying substrate at a variety of locations, and in a variety of shapes. They may be stacked on one another. Consequently, one can stack multiple therapeutic agents in multiple layers, which may emerge in series. As used herein a "layer" of a given material is a region of that material whose thickness is small compared to both its length and width. As used herein a layer need not be planar, for example, taking on the contours of an underlying substrate. Layers can be discontinuous (e.g., patterned). Terms such as "film," "layer" and "coating" may be used interchangeably herein.

Where polymeric regions are formed over all or only a portion of an underlying substrate, the underlying substrate may be formed from a variety of materials including metallic materials and non-metallic materials, such as ceramic materials, carbon-based materials, silicon-based materials, polymeric materials, and so forth. For example, a polymeric coating in accordance with the present invention, loaded with an antirestenotic agent, may be provided over a metallic stent.

To enhance coating integrity and stability (e.g., due to improved interaction at the interface between the coating and the substrate), it may be desirable in certain embodiments of the invention to dispose such polymeric regions on substrates that contain the same or related segments, for example, the same or related polyether segments, the same or related polyamide or polyurea segments, or a combination of both.

A specific example of a polyether-polyamide block copolymer, which is useful for medical device substrates, is a block copolymer that comprises a poly(tetramethylene oxide) segment and a polyamide-12 segment such as poly(tetramethylene oxide)-b-polyamide-12 block copolymer, available from Elf Atochem as PEBAX. Polyether-polyamide block copolymers such as PEBAX have excellent mechanical properties, are stable, and are readily processed (e.g., by melt or solution processing). Polyether-polyamide block copolymers such as PEBAX are also capable of forming good interfacial contacts with other materials including metals, ceramics and other polymers, particularly with polyethers, polyamides, and poly(ether-amide) copolymers. Hence, in certain embodiments of the invention, a medical device substrate containing a polyether-polyamide block copolymer (e.g., a PEBAX balloon) is provided with a polymer coating that contains a poly(ether amide) or poly(ether urea) in accordance with the present invention, for example, a copolymer containing a poly(tetramethylene oxide) soft segment and a uniform-length hard segment, such as one of the polyamide or polyurea segments described above.

Polymeric regions containing at least one polymer for use in the present invention may be formed using a variety of techniques, for example, from a solution that contains the following: (a) the polymer species making up the polymeric region and (b) at least one solvent species such as water, acetonitrile, ethanol, THF, methanol, among many others. If desired, various other agents may be added such as (c) at least one therapeutic agent, among many other possible agents. If the one or more of the polymer species making up the polymeric region have thermoplastic characteristics, then a melt may be formed, for example, from element (a) and optionally element (c). Such a solution or melt may then be applied to a substrate (e.g., an underlying medical device substrate or a detachable substrate such as a mold) by a variety of techniques including pouring, dipping, spraying, extrusion, coating with an applicator (e.g., by roller or brush), spin-coating, web coating, techniques involving coating via mechanical suspension including air suspension, ink jet techniques, electrostatic techniques, and combinations of these processes.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising a metallic substrate or a substrate that comprises a polymer selected from a polyether, a polyamide and a poly(ether amide), a polymeric region disposed over said substrate, and a therapeutic agent disposed within or beneath said polymeric region, said polymeric region regulating the release of said therapeutic agent from said medical device and comprising copolymer molecules each comprising a low $T_g$ segment displaying a $T_g$ that is below 20° C. (soft segment) and a uniform high $T_g$ segment displaying a $T_g$ that is above 50° C. (uniform hard segment), wherein said copolymer molecules are poly (ether amide) copolymer molecules, wherein said soft segment is a polyether soft segment, wherein said uniform hard segment is a uniform polyamide hard segment, wherein said polymeric region comprises polymer molecules that comprise covalently linked metallic or semi-metallic elements that form part of a ceramic network, and wherein said metallic or semi-metallic elements are covalently linked through a linkage that comprises the atomic sequence M-$C_x$—N—C—O—C, where $C_x$ is a carbon sequence comprising from 1 to 8 carbon atoms, and M is selected from Ti, Zr, Al, Ta, Zn, Mg, Fe and Ir.

2. The medical device of claim 1, wherein said metallic or semi-metallic elements are covalently linked to polymer molecules that comprise a polyether chain.

3. The medical device of claim 2, wherein said wherein said polyether chain comprises a plurality of units selected from —O—$(CH_2)_2$—, —O—$(CH_2)_3$—, —O—$(CH_2)_2(CH_3)$—, —O—$(CH_2)_4$—, and combinations of two or more of the same.

4. The medical device of claim 1, wherein said metallic or semi-metallic elements are covalently linked to polymer molecules that comprise a polyether chain and a polyamide chain.

5. The medical device of claim 1, wherein said metallic or semi-metallic elements are covalently linked to said copolymer molecules that comprise a soft segment and a uniform hard segment.

6. The medical device of claim 1, wherein said substrate comprises a polymer selected from a polyether, a polyamide and a poly(ether amide).

7. The medical device of claim 6, wherein said substrate comprises a polyether-polyamide block copolymer.

* * * * *

UNITED STATES PATENT AND TRADEMARK OFFICE
CERTIFICATE OF CORRECTION

| | | |
|---|---|---|
| PATENT NO. | : 8,440,214 B2 | Page 1 of 1 |
| APPLICATION NO. | : 11/344053 | |
| DATED | : May 14, 2013 | |
| INVENTOR(S) | : Michael Arney et al. | |

It is certified that error appears in the above-identified patent and that said Letters Patent is hereby corrected as shown below:

In the Claims:

Claim 3, col. 25, line 4, after "wherein said" remove "wherein said"

At claim 7, col. 25, line 21, add --8. The medical device of claim 1, wherein said substrate is a metallic substrate.--

Signed and Sealed this
Thirteenth Day of August, 2013

Teresa Stanek Rea
*Acting Director of the United States Patent and Trademark Office*